United States Patent [19]

Rubino

[11] 3,979,510

[45] Sept. 7, 1976

[54] ALUMINUM-ZIRCONIUM ANTI-PERSPIRANT SYSTEMS WITH COMPLEX ALUMINUM BUFFERS

[75] Inventor: Andrew M. Rubino, New Providence, N.J.

[73] Assignee: Armour Pharmaceutical Company, Phoenix, Ariz.

[22] Filed: June 7, 1974

[21] Appl. No.: 477,544

Related U.S. Application Data

[63] Continuation-in-part of Ser. Nos. 418,712, Nov. 23, 1973, and Ser. No. 431,639, Jan. 8, 1974, and Ser. No. 433,931, Jan. 16, 1974.

[52] U.S. Cl. .................................... 424/47; 424/66
[51] Int. Cl.$^2$............................................ A61K 7/32
[58] Field of Search ................... 424/46, 47, 66, 68

[56] References Cited

UNITED STATES PATENTS

| | | | |
|---|---|---|---|
| 2,923,660 | 2/1960 | Hallman............................ | 424/157 |
| 2,958,626 | 11/1960 | Schenck et al. ................... | 424/156 |
| 3,009,860 | 11/1961 | Grote................................. | 424/66 |
| 3,088,874 | 5/1963 | Geary et al. ...................... | 424/66 X |
| 3,725,540 | 4/1973 | Wall................................... | 424/46 |
| 3,773,683 | 11/1973 | Aubert............................... | 424/46 |

FOREIGN PATENTS OR APPLICATIONS

| | | | |
|---|---|---|---|
| 1,272,502 | 8/1961 | France................................ | 424/46 |
| 770,007 | 3/1954 | United Kingdom................. | 424/66 |

*Primary Examiner*—Dale R. Ore
*Attorney, Agent, or Firm*—Frank T. Barber; William W. Schwarze

[57] ABSTRACT

Anti-perspirant complexes are provided which comprise a combination of a basic aluminum compound, a zirconium compound and a complex aluminum buffering compound containing in addition to aluminum two or more of the following: magnesium, calcium, sodium, carbonate, sulfate, hydroxyl and water. The various components are present in the complex in amounts such that the Al/Zr mole ratio is about 10:1 to 1:10 and the pH of an aqueous solution containing 5 to 15 weight percent of the complex (based on the oxides of aluminum and zirconium) is at least about 3.

The basic aluminum compound may be any of the usual basic aluminum anti-perspirant salts, particularly the basic aluminum halides, and the zirconium compound may be a zirconium oxy salt and/or zirconium hydroxy salt. The complex aluminum buffer preferably contains among the additional groups or elements magnesium and/or carbonate. Examples of suitable complex aluminum buffers used include well-known antacid complexes such as hydrated magnesium aluminate, hydrated magnesium aluminum sulfate (HMAS), dihydroxy aluminum sodium carbonate (DASC), tetrahydroxy dialuminum magnesium carbonate (TDMC), and co-precipitates or co-dried mixtures of aluminum hydroxide with magnesium carbonate and/or calcium carbonate. The complexes may be used in conventional anti-perspirant forms, including aqueous solutions, aerosol sprays (including powder-in-oil aerosol sprays), as well as creams, lotions and cream sticks.

17 Claims, No Drawings

ALUMINUM-ZIRCONIUM ANTI-PERSPIRANT SYSTEMS WITH COMPLEX ALUMINUM BUFFERS

CROSS-REFERENCE TO RELATED APPLICATIONS

This application is a continuation-in-part of my following copending applications: Ser. No. 418,712, filed Nov. 23, 1973, entitled "Aluminum Zirconium Antiperspirant Systems With Salts of Amino Acids"; Ser. No. 431,639, filed Jan. 8, 1974, entitled "Zirconium-Aluminum-Polyol Buffered Anti-Perspirant Complexes"; and Ser. No. 433,931, filed Jan. 16, 1974, entitled "Aluminum-Zirconium Anti-Perspirant Systems With Hydroxy Carboxylic Compounds".

BACKGROUND OF THE INVENTION

The present invention relates to aluminum-zirconium anti-perspirant systems with complex aluminum buffers. More particularly, the invention is directed to water soluble complexes of zirconium which have a sufficiently high pH to be acceptable in anti-perspirant formulations for application to the human axilla.

It has been known in the art for some time that zirconium salts provide exceptionally effective anti-perspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an anti-perspirant has a pH of only about 0.8 and a solution of zirconyl hydroxy chloride which is effective as an anti-perspirant has a pH of only about 1.2. As a result, it is necessary to buffer these solution up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an anti-perspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley, 2,854,382 to Grad, and 3,792,068 to Luedders et al.) or aluminum hydroxy halides (see U.S. Pat. No. 2,906,668 to Beekman).

Recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

While the above attempts have succeeded in varying degrees in alleviating the acidic characteristics of zirconium salts, an entirely satisfactory zirconium anti-perspirant composition has not been previously found. Thus, it is desired to find a zirconium anti-perspirant composition which effectively makes use of the exceptional anti-perspirant properties of the zirconium, while at the same time offsetting the acidity and other disadvantages of zirconium salts.

SUMMARY OF THE INVENTION

According to the present invention, it has been found that effective anti-perspirant compositions may be achieved by forming a water soluble complex which comprises a combination of a basic aluminum compound, a zirconium compound selected from zirconium oxy salts, zirconium hydroxy salts and mixtures thereof, and a complex aluminum buffering compound containing in addition to aluminum at least two types of elements or groups selected from magnesium, calcium, sodium, carbonate, sulfate, hydroxyl and water. Such complex aluminum buffering compounds include particularly many of the well-known antacids. Preferably, the additional elements or groups should include magnesium and/or carbonate. These compounds should be present in the complex in such amounts as to yield an Al/Zr mole ratio of about 10:1 to 1:10, and preferably about 1:1 to 6:1, and should be such as to yield a pH of at least about 3 when the complex is placed in aqueous solution in an amount such that the solution contains about 5 to 15 weight percent of zirconium plus aluminum, calculated as the oxides.

The astringent complexes of the present invention may be obtained in solution or dry powder form. As a result, the complexes are satisfactory for use in any of a wide variety of conventional anti-perspirant forms, including lotions, creams, roll-ons, sticks, aerosol sprays, and the presently popular powder-in-oil sprays.

DETAILED DESCRIPTION OF PREFERRED EMBODIMENTS

The basic aluminum compounds which may be used in forming the complexes of the present invention include the conventional basic aluminum salts which have been known to the anti-perspirant art for some time, and which have a degree of anti-perspirant efficacy in their own right, as a result of the presence of the active aluminum ion. These basic aluminum salts may be represented by the following general empirical formula:

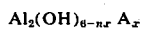

$$Al_2(OH)_{6-nx} A_x$$

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the 2/3 to 5/6 basic aluminum chlorides, in which A is chloride and $x$ is between about 1 and 2 and need not be an integer. Thus, such basic aluminum chlorides may be represented by the formulas

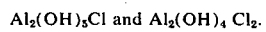

$$Al_2(OH)_5Cl \text{ and } Al_2(OH)_4Cl_2.$$

The basic aluminum chlorides are also referred to as aluminum chlorhydroxide or aluminum chlorhydrate or aluminum hydroxy chloride, and are commercially available from Reheis Chemical Company, Division of Armour Pharmaceutical Company under the trademark "Chlorhydrol".

In addition to the simple basic aluminum salts indicated above, complexes or derivatives of the basic aluminum salts may also be used advantageously in the complexes of the present invention. Examples of such derivatives or complexes include the phenolsulfonate derivatives described in U.S. Pat. No. 3,634,480 to Sheffield. Such complexes are formed by reacting 5/6 basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present specification.

The zirconium compounds which are useful in forming the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz} B_z$$

wherein $z$ may vary from about 0.9 to 2 and need not be an integer, $n$ is the valence of B, $2-nz$ is greater than or equal to O, and B may be the same as A in the general empirical formula for basic aluminum salts, that is B may be selected from the group consisting of halides, nitrate, sulfamate, sulfate and mixtures thereof. Although only zirconium compounds are exemplified in this specification, it will be understood that other Group IV B metals, including hafnium could be used to form the complexes of the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxyl group, varying from about 1.1 to only slightly greater than 0 groups per zirconium atom.

Particularly peferred zirconium compounds for use in the present invention include zirconyl chloride (also referred to as basic zirconium chloride or zirconium oxy chloride) and zirconyl hydroxy chloride, which may be represented by the simple formulas $ZrO Cl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g., hydrochloric acid. Other useful zirconium salts will be apparent to those of ordinary skill in the art, such as trioxodizirconium hydroxy halides and similar salts described, for example, in U.S. Pat. No. 2,837,400 to Blumenthal.

The particular complex aluminum buffering compounds which may be used to form the complexes of the present invention comprise aluminum complexes which contain in addition to aluminum two or more types of elements or groups of elements selected from magnesium, calcium, sodium, carbonate, hydroxyl, sulfate and water. Preferably, the complexes should contain magnesium ions or carbonate ($CO_3$) groups or both, along with one or more of the remaining additional elements or groups. Wherever the term "carbonate" is used herein, it will be understood that bicarbonate ($HCO_3$) may be included, since in many compounds and complexes the carbonate may be in the form of either the carbonate or the bicarbonate or both.

More particularly, the complex aluminum buffers used to form the anti-perspirant complexes of the present invention comprise the compounds of the above description which have been known and used in the past in connection with antacids and antacid preparations. Those of skill in aluminum chemistry, and particularly aluminum anti-perspirant and antacid technology, will readily understand that the above listed components of the complex aluminum compounds may be present in the compounds in many different amounts and forms, depending upon the particular preparation and other components present. That is, the exact structures of such complexes are not known, but can only be hypothesized. For example, just as the carbonate may be present in the compounds as either the carbonate or bicarbonate or both, water may be present in the compounds either as a hydroxyl group or water of hydration or water bound to the complex in some other manner.

Examples of two hydrated magnesium-aluminum compounds which may be used as the complex aluminum buffering compounds for making the compositions of the present invention are hydrated magnesium aluminum sulfate (HMAS) and hydrated magnesium aluminate (also known as magnesium aluminum hydrate or magaldrate). Both of these compounds are well known and both are commercially available. Alternatively, HMAS may be made according to the method described in U.S. Pat. No. 3,418,087 to Schenck, and hydrated magnesium aluminate may be made according to the method described in U.S. Pat. No. 2,923,660 to Hallman. The disclosures of both of these patents are incorporated herein by reference.

Examples of various complex aluminum compounds suitable for use in the present invention, and which contain carbonate groups, include a number of well-known antacids which comprise the reaction product of aluminum hydroxide ($Al(OH)_3$) with sodium carbonate, magnesium carbonate and/or calcium carbonate, or the corresponding bicarbonates. One example of such a carbonated aluminum complex is tetrahydroxy dialuminum magnesium carbonate (TDMC). The preparation of this compound is described in detail in U.S. Pat. No. 2,958,626 to Schenck et al., the disclosure of which is incorporated herein by reference. TDMC is also referred to as basic aluminum magnesium carbonate.

Although TDMC has been referred to above as the reaction product of aluminum hydroxide with a carbonate, it will be understood that such reaction product may be made according to any of the methods referred to in U.S. Pat. No. 2,958,626 or other methods known to the art. Thus, it is not necessary to start with aluminum hydroxide, but instead a metal aluminate or aluminum isopropoxide may be used. Similarly, magnesium bicarbonate and carbon dixoide may be used instead of magnesium carbonate. However, wherever used in the present specification and claims, the reference to a reaction product of aluminum hydroxide with sodium, magnesium or calcium carbonate will be understood to include any of these methods.

Another carbonate aluminum complex suitable for use in the present invention is dihydroxy aluminum sodium carbonate (DASC, which is also a well-known antacid and is available commercially. This complex may be made according to the processes disclosed in U.S. Pats. Nos. 2,783,124 and 2,783,127 to Grote. Alternatively, derivatives of DASC, such as those disclosed in U.S. Pat. No. 3,115,387 to Lewin, may also be used in the present invention. The disclosures of each of the above patents are incorporated herein by reference.

The largest class of carbonated aluminum complexes suitable for use as buffers in the complexes of the present invention is the antacids which are formed by co-drying or co-precipitating aluminum hydroxide, particularly the gel form, with magnesium carbonate or calcium cabonate. These carbonated aluminum complexes will be referred to herein as co-dried or co-precipitated reaction products. As used herein, the term "co-dried" refers to a process wherein already precipitated individual entities, such as aluminum hydroxide, magnesium carbonate, etc. in their gel forms, are mixed together in a slurry. The slurry is then dried to form a gel which is the co-dried reaction product. Since there is a certain amount of reaction between the entities and the water in the slurry, as well as some reaction during drying, the co-dried product is quite different from a product made by simply blending aluminum hydroxide and magnesium carbonate together in their dry form.

The basic patent describing the production of such codried reaction products is U.S. Pat. No. 2,797,978 to Beekman. Compounds of this type are also commercially available from Reheis Chemical Company Division of Armour Pharmaceutical Company under the name "F-MA-11", which is a specially co-dried mixture of aluminum hydroxide and magnesium basic carbonate.

As used herein, the term "co-precipitated" refers to a process in which aluminum compounds, magnesium or calcium compounds and carbonates are mixed together in a solution or suspension and then aluminum hydroxide and magnesium carbonate or calcium carbonate are precipitated together from such solution or suspension. The precipitation is caused by the adjustment of pH and/or other process conditions. By virtue of the fact that the various components of the final co-precipitated product are together in solution or suspension form, there is a much higher degree of reaction and bonding between the components of such products than in the case of co-dried products.

Another form of reaction is post-precipitation. In this reaction, one of the components, such as aluminum hydroxide is first precipitated, and then by adjusting the pH or other conditions, another component, such as magnesium carbonate, is precipitated on top of the aluminum hydroxide. Although the resulting reaction products of post-precipitation may be closer in the degree of bonding to co-dried products, such post-precipitated products will be referred to herein as co-precipitated reaction products.

Examples of co-precipitated products which may be used in the present invention are described in U.S. Pats. Nos. 2,880,136 to Gore; 3,239,416 to Rubino; and 3,272,703 to Rubino et al. The disclosures of each of these patents are incorporated herein by reference. In addition, the products described in the previously mentioned patents to Schenck, Grote and Hallman may also be referred to as co-precipitated reaction products.

The co-dried and co-precipitated reaction products of aluminum hydroxide with magnesium carbonate and/or calcium carbonate may also include other components. For example, the coprecipitates may also include hexahydric alcohols (hexitols), such as sorbitol and mannitol. Such modified co-precipitates are described in detail in U.S. Pat. No. 3,272,704 to Beekman, the disclosure of which is incorporated herein by reference. Other modified co-precipitates which may be used include those containing polyols, as described in copending application Ser. No. 252,816 of Rubino et al. for "Resuspendable Dried Antacids", now abandoned, the disclosure of which is also incorporated herein by reference. The latter resuspendable buffers are available commercially from the Reheis Chemical Company under the name "Rehydragels".

Still another group of modified co-precipitates useful in the present invention includes the hydroxy magnesium aluminum salts of amino aliphatic acids. Such modified co-precipitates are described in detail in U.S. Pat. No. 2,907,781 to Hermelin, the disclosure of which is incorporated herein by reference.

A number of other complex aluminum compounds having the above components, and traditionally used as antacids, may also be used as buffers in the complexes of the present invention. Such other compounds will be evident to those of ordinary skill in the art based upon this disclosure.

The particular amounts of each of the compounds to be added to form the complexes of the present invention may vary over a large range, depending upon the particular properties desired.

In general, the relative amounts of basic aluminum compound and zirconium compound to be added should be such as to yield an Al/Zr mole ratio of between about 10:1 and 1:10, and preferably about 1:1 to 6:1. Although greater amounts of zirconium would be desirable in the complex from the standpoint of antiperspirant efficacy, it will be appreciated that zirconium is considerably more expensive than aluminum. In addition, the greater the amounts of zirconium in the complex, the greater the acidity, and the greater the amount of the complex aluminum buffer compound which must be added to obtain a satisfactory pH.

The amount of the complex aluminum buffer to be added will also vary greatly depending upon the Al/Zr ratio, the particular buffer used, and the pH range which is desired for the particular astringent complex. In general, sufficient buffer should be added so that the pH of an aqueous solution of the complex at the normal cocentrations for anti-perspirant use will be at least about 3, and preferably in the range of about 3 to 5. The usual concentration of the complexes of the present invention for antiperspirant use will be such that a solution contains a total aluminum plus zirconium concentration of about 5 to 15 weight percent, with the aluminum and zirconium being calculated as the oxides (i.e., $ZrO_2$ and $Al_2O_3$).

If desired, the pH or the concentration of aluminum in the complexes of the present invention may be adjusted by adding aluminum chloride ($AlCl_3$) to the reaction mixture in the formation of the complexes of the present invention. Aluminum chloride, although quite acidic in solution, is well known for its anti-perspirant efficacy.

Among the advantages of the complexes of the present invention is that they are more basic and better buffers than the simple amino acid complexes previously used. Since the formation of complexes of the present invention results in increasing the pH of the highly acid zirconium systems, they can be used in smaller amounts than the simple amino acids to achieve the necessary pH levels for anti-perspirant use. In addition other ions known for their anti-perspirant activity as well as their basic character are introduced into the astringent complexes of the present invention. For example, the use of aluminum and co-dried mixtures including aluminum hydroxide results in the addition of more aluminum which is well known for its anti-perspirant activity.

The method of forming the complexes of the present invention is not particularly critical. In general, the complexes may be formed simply by adding the various components together in an aqueous solution and then, if desired, drying the solution to a dry powder. The various components are preferably added one at a time with stirring or agitation. Moderate heating, such as to a maximum of about 75° or 85° C. for up to a half hour may be advantageous after addition of certain ingredients, particularly when an insoluble compound is added or when a precipitate is formed after the addition of an ingredient. Where a water insoluble complex aluminum compound is being used, it is preferable to add this last.

The drying step is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes friable solid should be sufficient. If the complex is over dried, so that some of the coordinated and/or bound water is removed, the stability and/or activity of the complex may be interferred with, and the complex may not be redissolvable in solvents, particularly hydroalcoholic solvents.

While it has been indicated that the reaction process is not considered particularly critical, it will be understood that sufficient time, heat and agitation are needed to allow reaction of the salts to form the new complexes of the present invention. This is particularly so in the case of insoluble complex aluminum buffers which may be used to form complexes of this invention.

Although it has been indicated above that the drying step is not particularly critical, drying is nevertheless very important to the products of the present invention. Thus, it has been discovered that the drying process results in driving the buffer reaction more nearly to completion. That is, the pH of the final anti-perspirant complex in solution will be higher than would be expected from the pH of the solution during preparation prior to drying. Hence, it is strongly believed that the complexing reaction continues during drying, and this is evidenced by the fact that the pH of the reconstituted solutions in the following examples is higher than would be expected from the pH of the solutions before drying, even taking into consideration the different solution concentrations.

The complexes of the present invention will now be illustrated in more detail with reference to the following specific, non-limiting examples.

EXAMPLE I 2.87 parts per weight of a ZrO(OH)Cl solution containing 6.35% Zr were found to have a pH of 0.85. Addition of 0.1 part per weight of dihydroxy aluminum sodium carbonate (DASC), obtained commercially from Chattem Chemical Company, powder increased the pH to 1.0. The above solution was added to 28.1 parts per weight of aluminum chlorhydrate solution [$Al_2(OH)_5Cl$] containing 6% Al, which was heated to 80° C. prior to the addition. The final pH was 2.2 The solution was oven dried at 65° C. for 17-1/2 hours. A yellow crystalline solid was obtained, yielding the following assay: Al = 14.5%; Zr = 17.6%; Na = 0.23%; 15% pH (i.e. pH of a 15% w/w solution of the solid in water) = 3.45.

EXAMPLE II 0.2 part per weight of magnesium aluminum hydroxy carbonate-propylene glycol made according to copending application Ser. No. 252,816 and containing 13.1% Al, 17.2% Mg and 15.0% propylene glycol was added to 28.7 parts per weight of ZrO(OH)Cl solution containing 6.35% Zr, causing an increase in pH from 0.9 to 2.9. This turbid solution was then added to 28.1 parts per weight of $Al_2OH_5Cl$ solution (at 80°C.) containing 6.0% Al. A slightly turbid solution with a pH = 2.55 was formed. This solution was then oven dried at 65° C. for 17 ½ hours. A yellow crystalline solid was obtained, yielding the following assay: Al = 15.1%; Zr = 17.2%; Al:Zr::3:1, Mg = 0.6%; 15% pH = 3.3; 15% solution slightly turbid.

EXAMPLE III

To 13.8 parts per weight of $ZrOCl_2$ solution containing 13.2% Zr were added 6 grams of a magnesium aluminum hydroxy carbonate buffer [% Al = 22.8; % Mg = 1.68] made according to U.S. Pat. No. 2,797,978. 77.8 parts per weight of aluminum chlorhydrate [$Al_2(OH)_5Cl$] solution containing 4.35% Al were heated to 80° C. The above solution was then added slowly to the warmed aluminum chlorhydrate solution with agitation. The resulting solution was oven dried at 65° C. for 28 hours. A yellow crystalline solid was obtained, yielding the following assay: Al = 18.1%; Zr = 9.4%; Mg = 0.059%; 15% pH = 3.7.

EXAMPLE IV 0.5 part per weight of aluminum hydroxy carbonate-butylene glycol made according to copending application Ser. No. 252,816 and containing 23.4% Al and 15% butylene glycol was added to 13.8 parts per weight of $ZrOCl_2$ solution containing 13.2% Zr, causing an increase in pH from 0 to 0.2. The resultant solution was then slowly added to 82.8 parts per weight of $Al_2(OH)_5Cl$ solution at 80° C. containing 4.1% Al. A clear solution with a pH = 2.5 was obtained and then oven dried at 65° C. for 24 hours. A yellow crystalline solid was obtained, yielding the following assay: Al = 18.1%; Zr = 9.9%; Al:Zr::6:1, 15% solution = clear, 15% pH = 3.6.

EXAMPLE V

To 64.6 parts per weight of ZrO(OH)Cl solution containing 2.4% Zr was added 0.2 part per weight of a magnesium-aluminum-hydroxy-carbonate buffer made according to U.S. Pat. No. 2,797,978 and containing 24% $Al_2O_3$ and 27.9% MgO. The pH of the solution increased from 0.7 to 1.4. 27.0 parts per weight of aluminum chlorhydrate solution containing 12.5% Al were heated to 80° C. before the addition of the buffered zirconium solution commenced. The final pH of the solution was 2.8. The solution was oven dried at 65° C. for 24 hours. A white crystalline solid was obtained, yielding the following assay: Al = 17.7%, Zr = 10.7%; Mg = 0.48%; 15% pH = 4.0.

EXAMPLE VI

To 13.7 parts per weight of ZrO(OH)Cl containing 13.3% Zr was added 0.2 part per weight of an aluminum-magnesium-hydroxy-mannitol buffer made according to U.S. Pat. No. 3,272,704 and containing 10% Al, 10% Mg and 19.1% mannitol. The pH of the above solution increased from 0.55 to 1.1. The above solution was added to 77.9 parts per weight of aluminum chlorhydrate solution containing 4.35% Al. The pH of the solution decreased from 4.3 to 3.7. The solution was oven dried at 65° C. for 40 hours. A yellow crystalline solid was obtained yielding the following assay: Al = 3.94%; Zr = 10.9%; Mg = 0.13%; 15% pH = 3.86.

EXAMPLE VII 0.4 part per weight of an aluminum-magnesium-hydroxy sorbitol buffer made according to U.S. Pat. No. 3,272,704 and containing 13.2% Al, 6.78% Mg, and 27.8% sorbitol was added to 27.6 parts per weight of $ZrOCL_2$ solution containing 13.2% Zr. The above mixture was added slowly to an aluminum chlorhydrate solution containing 3.9% Al. The material was spray dried at 180° F. outlet at 180 ml/min. The material analyzed as: 13.3% Al, 14.3% Zr and 0.12% Mg. 15% pH = 3.2.

EXAMPLE VIII 0.2 part per weight $AL(OH)_3$-$CaCO_3$ made by a method according to Gore U.S. Pat. No. 2,880,136 and containing 15.2% Al and 11.5% Ca was added to 10 parts per weight $ZrOCl_2$ solution containing 13.2% Zr causing a rise in pH from 0 to 0.2. The resultant solution was then slowly added to 89.0 parts per weight of $Al_2(OH)_5Cl$ solution containing 4.7% Al. A clear solution with a pH = 3.4 was achieved, which was then oven dried at 65° C. for 18 hours. A yellow crystalline solid was obtained, yielding the following assay: Al = 20.0%; Zr = 6.7%; Al:Zr::10:1; Ca = 0.6%; 15% solution = slightly turbid; 15% pH = 3.85.

EXAMPLE IX 0.2 part per weight of hydrated magnesium aluminate (magaldrate) made according to U.S. Pat. No. 2,923,660 was added to 41.6 parts per wieght of $ZrOCl_2$ solution containing 13.2% Zr and the resultant cloudy solution was heated and held at 70° C. for 6 hours, then allowed to cool and stand for 16 hours. A cloudy solution with a pH = 0.1 was obtained. The above-mentioned solution was then slowly added to 61.4 parts per weight $Al_2(OH)_5Cl$ solution containing 2.8% Al. A cloudy solution with a pH = 2.4 was achieved, which was then oven dried at 65° C. for 48 hours. A white crystalline solid was obtained, yielding the following assay: Al = 7.2%; Zr = 24.0%; Al:Zr::1:1; Mg = 0.2%; 15% solution = slight tint; 15% pH = 3.35.

EXAMPLE X 0.4 part per weight hydrated magnesium aluminum sulfate (HMAS) made according to U.S. Pat. No. 3,418,087 and containing 13.8% Al, 9.4% Mg and 11.1% $SO_4$ was added to 41.2 parts ZrO(OH)Cl solution containing 13.3% Zr causing a rise in pH from 0.45 to 0.75. The resultant solution was then slowly added to 94.8 parts per weight of $Al_2(OH)_5Cl$ solution containing 3.6% Al. A slightly hazy solution with a pH = 3.2 was achieved, which was then oven dried at 65° C. for 24 hours. A yellow crystalline solid was obtained, yielding the following assay: Al = 12.7%; Zr = 21.4%; Al:Zr::2:1; Mg = 0.16%; 15% solution = slight haze; 15% pH = 3.65.

EXAMPLE XI 0.2 part per weight calcium aluminum hydroxy carbonate made according to U.S. Pat. No. 3,272,703 and containing 10.1% Al and 24.6% CA was added to 10.0 parts per weight $ZrOCl_2$ solution containing 13.2% Zr causing a rise in pH from 0 to 0.25. The resultant solution was then slowly added to 89.0 parts per weight $Al_2(OH)_5Cl$ solution containing 4.7% Al. A clear solution with a pH = 3.4 was achieved, which was then oven dried at 65° C. for 40 hours. A clear crystalline solid was obtained, yielding the following assay: Al = 19.5%; Zr = 6.8%; Al:Zr::10:1; Ca = 0.23%; 15% solution - clear; 15% pH = 3.8.

As indicated previously, the complexes of the present invention may be used in a variety of conventional anti-perspirant forms which are applied to the human axilla for effective perspiration inhibition. In such fomrulations, the complex should be present in such amounts that the total aluminum plus zirconium content of the formulation is between about 1.5 and 15 weight percent (depending on the type of formulation employed), calculated as the oxides of the aluminum and zirconium.

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic solvents, the complexes of the present invention should be present in the above antiperspirant forms in amounts such that the total content of aluminum plus zirconium in the formulation is on the order of about 5 to 15 weight percent (calculated as the oxides of aluminum and zirconium) or 10 to 30 weight percent of the active ingredient (calculated on a solids basis).

The complexes of the present invention may also be used in the now popular powder-in-oil aerosol sprays. The powder-in-oil systems comprise the dispersion of a finely divided anti-perspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical anti-perspirant formulations employing the complexes of the present invention are exemplified in Table I.

The present invention may be embodied in other specific forms without departing from the spirit or essential attributes thereof and, accordingly, reference should be made to the appended claims, rather than to the foregoing specification as indicating the scope of the invention.

$$ZrO(OH)_{2-nz}B_z$$

wherein $z$ may vary from 0.9 to 2, $n$ is the valence of B, $2-nz$ is greater than or equal to 0, and B is selected from the group consisting of halide, nitrate, sulfamate, sulfate and mixture thereof; and c. a complex aluminum buffer compound selected from the group consisting of hydrated magnesium aluminate, hydrated magnesium aluminum sulfate, and the co-dried or co-precipitated reaction product of aluminum hydroxide with a carbonate selected from the group consisting of magnesium carbonate, calcium carbonate, sodium carbonate and mixtures thereof;

said basic aluminum and zirconium compounds being present in such amounts as to yield an Al/Zr mole ratio of about 10:1 to 1:10, and said buffer compound being

TABLE I

ANTIPERSPIRANT FORMULATIONS

| Ingredient | A*<br>Powder-in-oil<br>Aerosol | B*<br>Powder-in-oil<br>extra-dry<br>Aerosol | Parts by Weight<br>C<br>Spray<br>(Manual-Pump) | D<br>Oil-in-water<br>lotion | E<br>Oil-in-water<br>cream |
|---|---|---|---|---|---|
| Active Ingredient (Antiperspirant) | | | | | |
| Complex of Example II | 3.5 | | | | |
| Complex of Example IV | | | 10.0 | | |
| Complex of Example III | | 5.0 | | | |
| Complex of Example XI | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane) | 45.0 | 45.0 | | | |
| Water | | | 19.5 | 66.0 | 56.0 |
| Alcohol SD-39C | | | 55.0 | | |
| Talc, U.S.P. | | 1.5 | | | |
| Arlacel 165 (4) | | | | 5.0 | 18.0 |
| Amerchol L-101 (2) | | | | 2.0 | |
| Solulan 98 (2) | | | | 4.0 | |
| Myrj 52 (4) | | | | 2.0 | |
| Cetyl Alcohol | | | | 2.0 | 5.0 |
| Glycerin | | | | 1.0 | |
| Veegum HV (3) | | | | q.s. | q.s. |
| Preservative | | | | | 5.0 |
| Spermaceti | | | | | 1.0 |
| Titanium Dioxide | | | | | |

(1) Cab-O-Sil M-5 — fumed amorphous silica of Cabot Corp.
(2) Amerchol L-101 and Solulan 98 — lanolin derivatives of Amerchol, Inc.
(3) Veegum HV — product of R. T. Vanderbilt & Co.
(4) Arlacel 165 and Myrj 52 — non-ionic emulsifiers of ICI America.
*For "powder-in-oil" aerosols, active ingredient powders are ground in a micronizer before use to yield powders containing a particle size greater than 97% through a 325 mesh screen (44u).

I claim:
1. An astringent, water soluble complex formed by reacting the following components (a), (b) and (c) in aqueous medium:

a. a basic aluminum compound selected from the group having the general empirical formula:

$$Al_2(OH)_{6-nx} A_x$$

wherein $x$ may vary from greater than 0 to less than 6, $6-nx$ is greater than or equal to 0, $n$ is the valence of A, and A is selected from the group consisting of halide, nitrate, sulfamate, sulfate and mixture thereof;

b. a zirconium compound selected from trioxodizirconium salts and the group having the general empirical formula:

present in such an amount that the pH of a 5 to 15 weight percent (based on the oxides of Al and Zr) aqueous solution of the complex is at least about 3.

2. A complex according to claim 1 wherein x varies from about 1 to about 2.

3. A complex according to claim 1 wherein A is chloride or bromide.

4. A complex according to claim 1 wherein the basic aluminum compound is a phenolsulfonate complex of said basic aluminum compound.

5. A complex according to claim 1 wherein B is chloride and z is about 1.

6. A complex according to claim 1 wherein B is bromide and z is about 1.

7. A complex according to claim 1 wherein said complex aluminum buffer is hydrated magnesium aluminate or hydrated magnesium aluminum sulfate.

8. A complex according to claim 1 wherein said reaction poduct comprises a co-dried mixture of aluminum hydroxide with magnesium carbonate, calcium carbonate or mixtures thereof.

9. A complex according to claim 1 wherein said reaction product comprises dihydroxy aluminum sodium carbonate.

10. A complex according to claim 1 wherein said reaction product comprises tetrahydroxy dialuminum magnesium carbonate.

11. A complex according to claim 1 wherein the Al/Zr mole ratio is about 1:1 to 6:1.

12. A complex according to claim 1 wherein said complex also includes aluminum chloride.

13. A complex according to claim 1 wherein said complex is in the form of a powder.

14. A complex according to claim 1 wherein said reaction product also includes a hexitol selected from the group consisting of mannitol and sorbitol.

15. A complex according to claim 1 wherein said reaction product also includes a polyol.

16. An anti-perspirant composition comprising an aqueous solution of the complex according to claim 1 wherein said complex is present in an amount such that the total amount of aluminum plus zirconium in the solution, calculated as the oxides, is about 5 to 15 weight percent.

17. A powder-in-oil anti-perspirant composition comprising an aerosol propellant, oil and the complex according to claim 13 wherein said complex is present in an amount of about 1–6 weight percent of the anti-perspirant composition.

* * * * *